United States Patent [19]

Bates et al.

[11] Patent Number: 5,957,932
[45] Date of Patent: Sep. 28, 1999

[54] CALCULUS REMOVAL

[75] Inventors: James S. Bates, Bloomington; Randall L. Hacker, Martinsville, both of Ind.

[73] Assignee: Boston Scientific Corporation, Natick, Mass.

[21] Appl. No.: 09/072,316

[22] Filed: May 4, 1998

Related U.S. Application Data

[63] Continuation of application No. 08/640,156, Apr. 30, 1996, Pat. No. 5,788,710.

[51] Int. Cl.⁶ ..................................................... A61B 17/22
[52] U.S. Cl. ............................................. 606/127; 606/113
[58] Field of Search ............................... 606/1, 110, 113, 606/114, 127, 128, 205–211

[56] References Cited

U.S. PATENT DOCUMENTS

| | | |
|---|---|---|
| 1,310,982 | 7/1919 | Davis . |
| 1,517,787 | 12/1924 | Langbein . |
| 1,612,697 | 12/1926 | Cecil . |
| 1,677,671 | 7/1928 | Councill . |
| 2,113,246 | 4/1938 | Wappler . |
| 2,487,502 | 11/1949 | Willinsky . |
| 2,556,783 | 6/1951 | Wallace . |
| 3,181,533 | 5/1965 | Heath . |
| 3,314,431 | 4/1967 | Smith, Jr. et al. . |
| 3,620,212 | 11/1971 | Fannon, Jr. et al. . |
| 3,739,784 | 6/1973 | Itoh . |
| 3,890,977 | 6/1975 | Wilson . |
| 4,614,187 | 9/1986 | Mulhollan et al. . |
| 4,625,726 | 12/1986 | Duthoy . |
| 4,633,871 | 1/1987 | Shinozuka . |
| 4,655,219 | 4/1987 | Petruzzi . |
| 4,665,906 | 5/1987 | Jervis . |
| 4,688,555 | 8/1987 | Wardle . |
| 4,741,335 | 5/1988 | Okada . |
| 4,763,669 | 8/1988 | Jaeger . |
| 4,768,505 | 9/1988 | Okada et al. . |
| 4,880,015 | 11/1989 | Nierman . |
| 4,944,741 | 7/1990 | Hasson . |
| 4,945,920 | 8/1990 | Clossick . |
| 5,059,199 | 10/1991 | Okada et al. . |
| 5,098,440 | 3/1992 | Hillstead .................................. 606/108 |
| 5,152,279 | 10/1992 | Wilk . |
| 5,163,942 | 11/1992 | Rydell . |
| 5,174,300 | 12/1992 | Bales et al. . |
| 5,192,008 | 3/1993 | Hwan . |
| 5,197,968 | 3/1993 | Clement . |
| 5,209,747 | 5/1993 | Knoepfler . |
| 5,251,638 | 10/1993 | Cottone, Jr. et al. . |
| 5,254,130 | 10/1993 | Poncet et al. . |
| 5,290,294 | 3/1994 | Cox et al. . |
| 5,311,858 | 5/1994 | Adair . |
| 5,334,208 | 8/1994 | Soehendra et al. . |
| 5,370,282 | 12/1994 | Sedlmeier . |
| 5,417,203 | 5/1995 | Tovey et al. . |
| 5,425,743 | 6/1995 | Nicholas . |
| 5,658,296 | 8/1997 | Bates et al. .............................. 606/127 |

FOREIGN PATENT DOCUMENTS

| | | |
|---|---|---|
| 0 160 870 A3 | 11/1985 | European Pat. Off. . |
| 0 337 918 A1 | 10/1989 | European Pat. Off. . |
| 450 608 A1 | 10/1991 | European Pat. Off. . |
| 0 484 671 A3 | 5/1992 | European Pat. Off. . |
| 0 484 671 A2 | 8/1992 | European Pat. Off. . |
| 0 538 984 A3 | 4/1993 | European Pat. Off. . |
| 0 555 103 A1 | 8/1993 | European Pat. Off. . |
| 0 565 049 A1 | 10/1993 | European Pat. Off. . |
| 0 571 057 A1 | 11/1993 | European Pat. Off. . |

(List continued on next page.)

OTHER PUBLICATIONS

Falk et al., United States Statutory Invention Registration, Reg. No. H1028, Mar. 3, 1992, United States Patent Office, Washington DC.

*Primary Examiner*—Glenn K. Dawson
*Attorney, Agent, or Firm*—Testa, Hurwitz & Thibeault, LLP

[57] ABSTRACT

Grasping an object, e.g., a calculus in the biliary tract, using a grasper, such as a basket, that can be opened and closed without mechanical advantage and also rotated about the device axis to make it easier to capture the object. The basket can then be closed further with mechanical advantage to crush the object.

6 Claims, 4 Drawing Sheets

FOREIGN PATENT DOCUMENTS

| | | |
|---|---|---|
| 0 598 607 A3 | 5/1994 | European Pat. Off. . |
| 24 28 319 | 1/1976 | Germany . |
| 32 06 846 A1 | 9/1983 | Germany . |
| 33 40 581 C1 | 6/1985 | Germany . |
| 35 21 717 A1 | 12/1985 | Germany . |
| 34 40 889 C1 | 6/1986 | Germany . |
| 86 04 065 | 7/1986 | Germany . |
| 36 03 344 A1 | 8/1986 | Germany . |
| 8707515 U1 | 9/1987 | Germany . |
| 37 09 706 A1 | 10/1987 | Germany . |
| 8707516 U1 | 10/1987 | Germany . |
| 37 14 560 A1 | 11/1987 | Germany . |
| 37 04 094 A1 | 8/1988 | Germany . |
| 37 09 067 A1 | 9/1988 | Germany . |
| 37 39 254 A1 | 6/1989 | Germany . |
| 40 24 636 A1 | 2/1992 | Germany . |
| 41 31 176 A1 | 4/1993 | Germany . |
| 42 12 430 A1 | 10/1993 | Germany . |
| 61-9601 | 3/1986 | Japan . |
| 63-197443 | 8/1988 | Japan . |
| 990 220 | 1/1983 | U.S.S.R. . |
| 2 151 142 | 12/1983 | United Kingdom . |
| WO 91/02493 | 3/1991 | WIPO . |
| 92/05828 | 4/1992 | WIPO . |
| WO 94/05223 | 3/1994 | WIPO . |
| 95/05129 | 2/1995 | WIPO . |

FIG. 5a

CALCULUS REMOVAL

This is a continuation of U.S. application Ser. No. 08/640,156, filed Apr. 30, 1996, now U.S. Pat. No. 5,788,710.

FIELD OF THE INVENTION

This invention relates to removing calculi and other objects.

BACKGROUND OF THE INVENTION

In a stone retrieval procedure, a calculus (stone) is removed from, e.g., the bile duct using a catheter device that is passed through an endoscope. The catheter device includes a collapsible basket that is extended from a sheath to capture the stone for removal.

In a lithotripsy procedure, the stone is crushed either to facilitate natural passage or to facilitate removal with a basket. This procedure can be performed with a catheter device that can apply large collapsing force to the basket, which crushes the captured stone. Many other medical procedures also involve grasping, sampling, removal, and/or crushing objects in the body.

SUMMARY OF THE INVENTION

In an aspect, the invention features an instrument for treating an internal organ which is obstructed by a calculus. The instrument includes an elongate catheter sheath extending along an axis from a proximal end to a distal end that is sized for insertion into the organ. A basket-form calculus grasper is formed of flexible wires and adapted to be extended from and withdrawn within the distal end of the catheter sheath such that, when extended from the distal end of the sheath, the wires are spaced to permit passage of the calculus and when withdrawn at least partially into the sheath, the wires collapse in a manner to capture the calculus. A tension element is coupled to the grasper. A handle at the proximal end of the catheter sheath receives the tension element and houses an operating assembly. The operating assembly permits application of axial force to the tension element for extending or withdrawing the grasper from the distal end of the sheath and permits rotating the grasper about the axis. The operating assembly includes a manual actuator and a mechanical actuator. The manual actuator is coupled to the tension element and arranged for applying axial force to the tension element for extending the grasper from the distal end of the sheath and for imparting rotational motion to the tension element for rotating the grasper about the instrument axis to a desired orientation. The mechanical actuator is arranged to apply axial force to the tension element for withdrawing the grasper with mechanical advantage.

In another aspect, the invention features an operating handle for a medical instrument. The operating handle includes a control element extending along an axis and an operating assembly which is coupled to the control element. The operating assembly includes a manual actuator directly connected to the control element for moving the control element axially and for rotating the control element about the axis to a desired orientation. The operating assembly also includes a mechanical actuator coupled to the control element through a selective engagement member, such that the mechanical actuator is actuatable to move the control element axially with mechanical advantage and without rotation from the desired orientation.

In another aspect, the invention features an instrument for grasping or crushing a calculus. The instrument includes an elongate catheter sheath that extends along an axis from a proximal end to a distal end and is sized for insertion into the organ. A basket-form calculus grasper is formed of flexible wires arranged to be extended from and withdrawn within the distal end of the catheter sheath such that, when extended from the distal end of the sheath, the wires are spaced to permit passage of the calculus and when withdrawn at least partially into the catheter sheath, the wires collapse in a manner to capture the calculus. A tension element is coupled to the grasper. A handle is provided at the proximal end of the catheter sheath that receives the tension element and houses an operating assembly to apply axial force to the tension element for extending or withdrawing the grasper from the distal end of the sheath and for rotating the grasper about the axis. The operating assembly includes a manual control knob directly connected to the tension element and arranged for applying axial force to the tension element for extending the grasper from the distal end of the sheath and for imparting rotational motion to the tension element for rotating the grasper about the instrument axis to a desired orientation. A mechanical actuator is arranged to apply axial force to the tension element for withdrawing the grasper with mechanical advantage. The mechanical actuator includes an engaging piece cooperatively constructed with the tension element to bear on the tension element to apply axial force when the tension element is in various rotational states.

Embodiments may include one or more of the following features. The tension element has a substantially smooth cylindrical surface and the engaging piece is a jam element arranged to bear on the surface. The instrument includes a ratchet mechanism for selectively preventing extension of the basket. The ratchet mechanism includes a ratchet jam element arranged to bear on the surface. The mechanical actuator includes a failure element that fails mechanically in response to excessive tension applied to the tension element while permitting actuation of the grasper using the manual control knob. The failure element is a hinge. The hinge is a weakened portion on the mechanical actuator jam element.

Embodiments may include one or more of the following features. The tension element has an outer engaging surface along a segment corresponding to a desired range of rotation and the mechanical actuator includes a complementary engaging element for applying axial withdrawing force. The outer engaging surface and the engaging element are cooperatively constructed to permit the engaging element to apply the axial force to the tension element with the tension element rotationally oriented within the range. The outer engaging surface is a substantially smooth cylindrical surface. The engaging element is a jam element. The jam element is biased in a non-engaging configuration to permit manual operation of the basket using the manual actuator without interference from the mechanical actuator and the jam element can be operated against the bias to engage the tension element for applying axial force to the tension element with mechanical advantage. The jam element is operated through a trigger.

Embodiments may also include one or more of the following features. The instrument includes a ratchet mechanism for preventing extension of the basket. The ratchet mechanism includes an engaging piece cooperatively constructed with the tension element to permit the engaging piece to engage the tension element with the tension element rotationally oriented within the range. The ratchet engaging piece is a ratchet jam element. The ratchet jam element can be operated to a non-engaging configuration to permit operation using the manual control without interference from the ratchet mechanism.

Embodiments may also include one or more of the following features. The manual actuator is actuatable to apply axial force to the tension element for extending and withdrawing the grasper. The catheter sheath is sized to pass through an endoscope. The device includes a fluid port in communication with the catheter sheath. The control element is extended and withdrawn relative to a sheath.

In another aspect, the invention features a method of grasping an object in a body. The method includes providing a medical instrument having an instrument axis and including a grasper actuatable between an open and closed condition. The medical instrument includes an operating mechanism for actuating the grasper alternatively with mechanical advantage or without mechanical advantage and for rotating the grasper about the axis. The grasper is positioned in proximity to the object. The grasper is actuated to open the grasper. The grasper is rotated to a desired orientation and manipulated about the object. The grasper is actuated with mechanical advantage to close the grasper.

Embodiments may also include one or more of the following features. The grasper is actuated with mechanical advantage without rotation of the grasper from the desired orientation. The device is delivered through an endoscope. The object is a calculus.

Embodiments of the invention may provide one or more of the following advantages. Embodiments of the device may be operated to simply grasp, as well as to grasp and crush a calculus. For calculus grasping, the basket can be opened, rotated, and closed manually, without mechanical advantage or interference from a mechanical operating assembly, which improves the tactile feedback to the user and makes the grasping operations easier. For calculus crushing, the basket can be closed with mechanical advantage to apply large collapsing forces. The crushing operation can be conducted without changing the rotational orientation of the basket. Accordingly, calculus treatment, with or without crushing, can be accomplished quickly, even in cases where stones are positioned in a manner which would make capture difficult without basket rotation. In addition, the operating assembly has a mechanically-efficient, low-cost design that is preassembled and permits single-use embodiments, i.e. they can be disposed after a procedure. The operating mechanism may be configured for one-handed crushing operation.

Further aspects, features, and advantages follow.

DESCRIPTION OF THE PREFERRED EMBODIMENT(S)

We first briefly described the drawings.

DRAWINGS

FIG. 5 is a perspective view of a jam element of the operating assembly, while

DESCRIPTION

Figure 1:
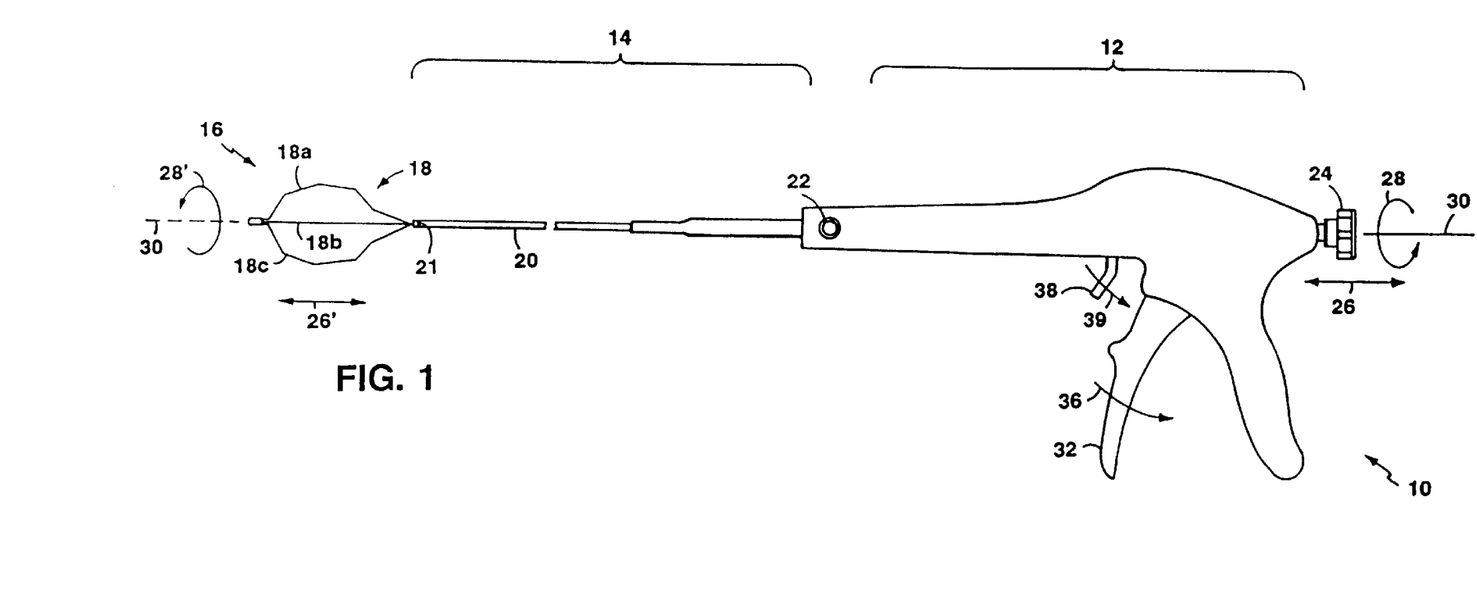
FIG. 1 is a side view of an instrument for grasping or crushing a calculus.

Referring to FIG. 1, in an embodiment, an instrument 10 for removing intact or crushing a calculus includes a handle portion 12, a catheter portion 14, and a grasper portion 16. The grasper portion 16 is a basket 18 formed of resilient wires 18a, 18b, 18c, (three of four wires shown) which, when extended from the catheter portion 14, spring outwardly to provide open space between the wires through which a calculus can pass. When the grasper 16 is withdrawn into the catheter portion 14, the wires collapse about the calculus.

The basket 18 is controlled through an operating assembly housed in the handle portion 12. The operating assembly includes a manual control knob 24, a trigger 32, and a ratchet switch 38. The manual control knob 24 is directly connected to the basket so that when the control knob is extended, retracted (arrow 26), or rotated (arrow 28) about the device axis 30, the basket is extended, retracted (arrow 26'), or rotated (arrow 28') by the same amount without mechanical advantage.

The trigger 32 is coupled to the basket through a mechanism so that it can be actuated (arrow 36) to retract the basket with mechanical advantage, permitting the operator to apply considerable collapsing force to the basket in order to crush a calculus.

The ratchet switch 38 permits selective engagement and disengagement of a ratchet stop. By pulling the ratchet switch (arrow 39), the grasper 16 can be actuated and rotated manually using the control knob 24 without interference from the ratchet (or the mechanism associated with the trigger 32). When the ratchet switch 38 is released, the ratchet becomes engaged to prevent extension of the basket so that successive actuation of the trigger 32 will increase the collapsing force of the basket.

Figure 2:
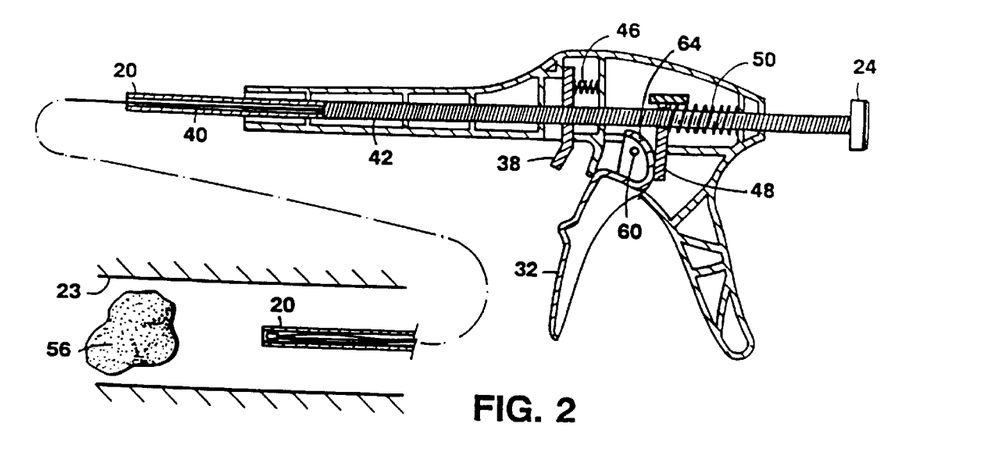
FIGS. 2–2c are cross-sectional side views illustrating the structure and use of the instrument in FIG. 1.
Figure 2A:
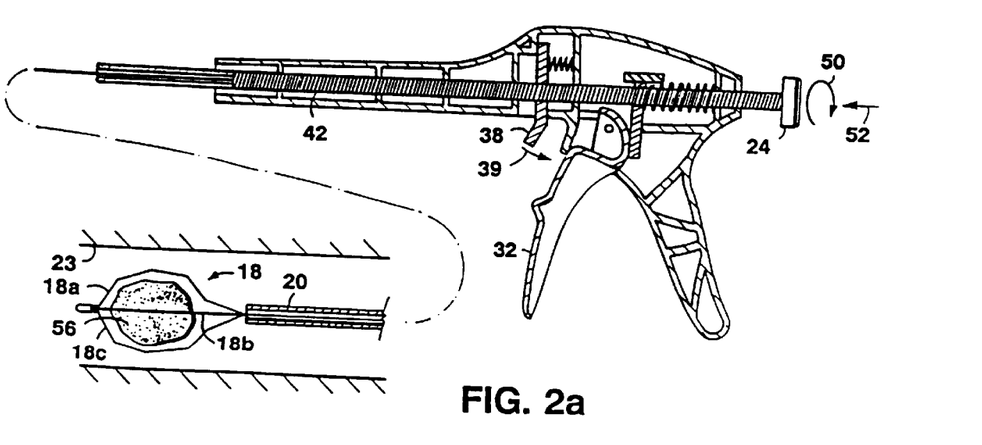
Figure 2B:
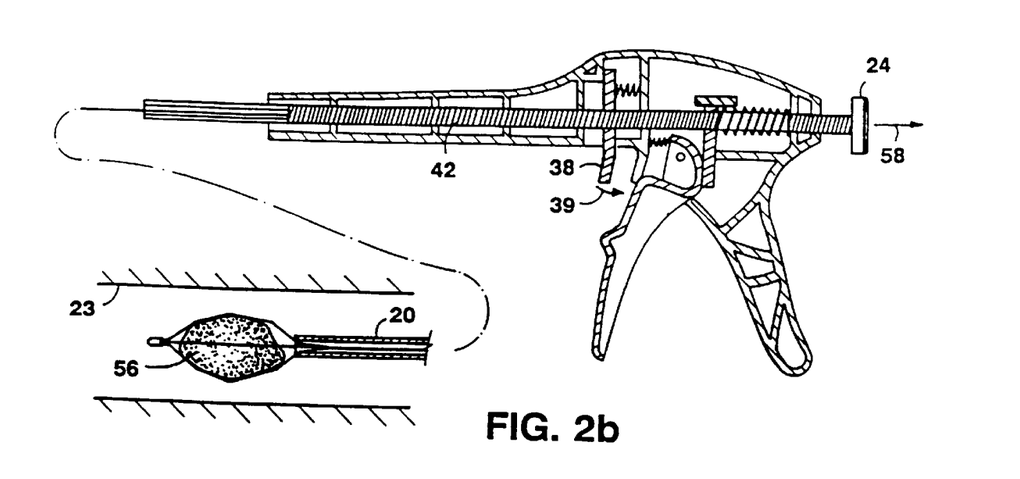
Figure 2C:
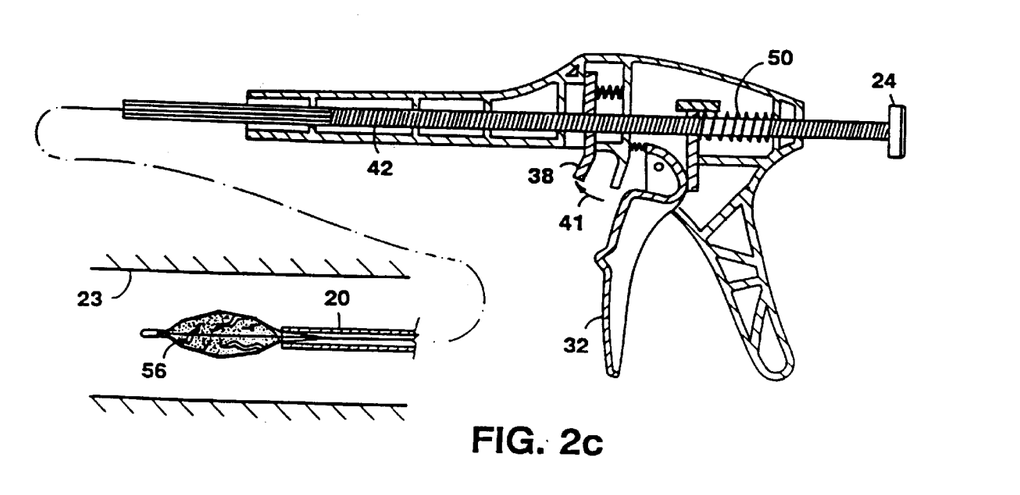

Referring to FIGS. 2–2c, the basket 18 is connected to a tension cable 40 which extends through a catheter sheath 20. At its proximal end, the tension cable 40 is attached to a smooth-surfaced cylindrical handle rod 42 which is coupled to the operating assembly housed within the handle portion 12. The manual control knob 24 is connected to the proximal end of the handle rod 42. The retracting key 48 and the ratchet switch 38 are constructed to bear on the smooth-surfaced handle rod to control its motion regardless of the rotational orientation of the rod and, hence, the basket.

The ratchet switch 38 and retracting key 48 are jam elements that have an aperture through which the handle rod 42 can pass with slight clearance. When the keys are oriented at a slight angle with respect to the axis of the handle rod 42, they bear on and grip the handle rod 42. The switch 38 and retractor key 48 are biased in preferential orientations by springs 46, 50, respectively. The ratchet switch 38 is biased to grip the handle rod 42, thus preventing extension or rotation (but permitting withdrawal). The retractor key 48 is biased such that it does not substantially frictionally grip the handle rod 42 and is tilted into gripping condition by actuation of trigger 32.

The trigger 32 pivots about a pin 60 and includes an eccentric cam surface 64. As the trigger 32 is actuated, the cam surface 64 bears on the retractor key 48, causing the retractor key to tilt slightly and grip the handle rod 42 with substantial friction. As the trigger is actuated further, the handle rod 42 and the basket 18 are pulled into the sheath with a 4:1 mechanical advantage from the operator's hand to the force applied to the basket. When the trigger 32 is released, spring 50 causes the retractor key 48 to return to the untilted, non-gripping condition and slides the retractor key forward along the handle rod 42 which at the same time pushes the trigger 32 to its original condition. Forward motion of the handle rod 42 and the basket is prevented by the ratchet key 38 which maintains grip on the handle rod 42. Accordingly, by actuating the trigger 32 a number of times, the basket 18 is pulled further into the sheath 20 which increases the collapsing force of the basket wires which crush the calculus.

Referring particularly to FIGS. 2 and 2a, the device is delivered through an endoscope (not shown) into a body cavity 23 with the basket 18 retracted within the sheath 20 (FIG. 2). The distal end of the catheter sheath 20 is located in the region of a calculus 56 and the ratchet switch 38 is pulled proximally (arrow 39), which frees it from the gripping relationship with the handle rod 42 (FIG. 2a). The basket 18 is then projected from the end of the sheath by pushing the manual control knob 24 (arrow 52) causing the basket wires to spread. The basket 18 can be rotated (arrow 50) about the device axis using the control knob 24 to capture the calculus 56 between the wires.

Referring particularly to FIG. 2b, the basket 18 can then be at least partially withdrawn into the sheath 20 by pulling control knob 24 proximally (arrow 58). The basket wires thus collapse about the calculus 56. In cases where the calculus is smaller than the outer diameter of the endoscope, the basket, grasping the calculus, can be withdrawn with the endoscope and removed from the body.

In cases in which the calculus is larger than the diameter of the endoscope, the operator can use the device to crush the calculus. Calculus crushing can also be useful in cases where multiple stones are present. Stones can be crushed and left in the lumen to be flushed naturally from the body. In this manner, multiple introductions and withdrawals of the device can be avoided. Basket rotation, as provided by the device, also makes it easier to remove a crushed stone from the basket while the device remains inside the body.

Referring as well to FIG. 2c, for a crushing operation, the user withdraws the manual control knob 24 to collapse the basket wires tightly about the calculus 56. The operator then releases the ratchet switch 38 (arrow 41) which causes the switch to be biased by the spring 46 into the gripping orientation, preventing the basket from being extended. The calculus can be crushed by applying additional collapsing force to the basket using the trigger 32.

Figure 3:
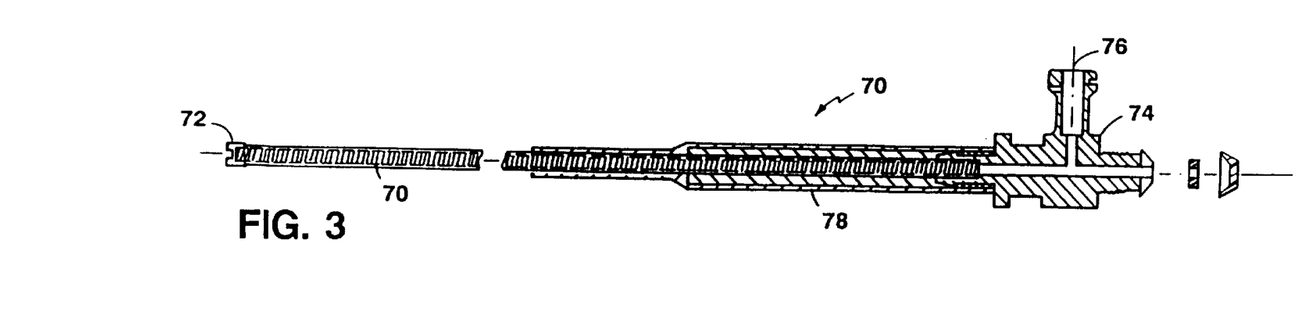
FIG. 3 is a cross-sectional view of a catheter body for use with the instrument in FIG. 1.

Referring to FIG. 3, in a particular embodiment, the catheter sheath 20 is made of a stainless steel coil 70 that is covered by fluorothylene polymer (FEP) heat shrink, which enhances lubricity to protect the interior of the endoscope during device delivery. The end of the coil includes a stainless steel tip 72 against which the basket wires bear as they are retracted. A low friction PTFE polymer tube (not shown) is provided inside the coil to enhance lubricity during high tension stone-crushing with the catheter around a tight bend. The proximal end of the sheath 20 includes a luer t-fitting 74 with a port 76 through which fluid can be injected. Referring as well to FIG. 1, the handle portion 12 includes an injection port 22 that communicates with the t-fitting in a manner that fluid, such as saline or contrast, can be delivered through the catheter portion to flow from the distal end of the catheter 20. A piece of heat shrink tubing 78 is provided about the proximal portion of the sheath to provide a fluid-tight seal. The catheter sheath 20 has a length of about 180 cm, an outer diameter of about 2.7 mm, and an inner diameter of about 1.7 mm. This embodiment is sized to pass through a 3.2 or 2.8 mm diameter endoscope channel.

Figure 4:
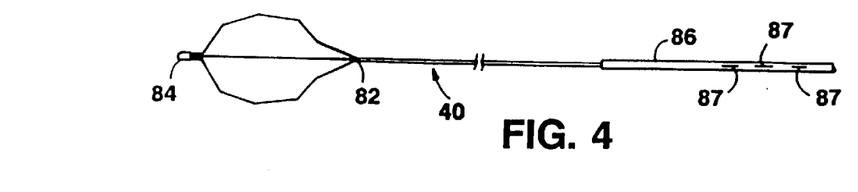
FIG. 4 is a side-view of a basket and tension wire arrangement.

Referring to FIG. 4, the tension cable 40 is a 4×7 stainless steel cabled wire. A short (2–3 mm) stainless steel canula 82 is provided over the tension cable and soldered to keep the wires from unraveling. Distal of the canula 82, four 1×7 cables are separated to form the basket wires. The wires are plasma welded together at their distal ends inside a stainless steel tip 84. The proximal end of the cabled wire 80 includes a canula 86 which is slipped onto the cable, held in place with solder (applied through slits 87) and welded. The basket 18 is connected to the handle rod 42 (stainless steel) by drilling a lumen in the distal end of the handle rod, inserting the proximal end of the cable, and plasma welding.

The handle body and trigger are made of injection molded plastic in a clam-shell configuration. The ratchet key 38 and the retractor key 48 are formed of stainless steel (17-4) with a circular aperture having a diameter of 0.25 inch. The outer diameter of the handle rod is about 0.249 inch.

Figure 5:
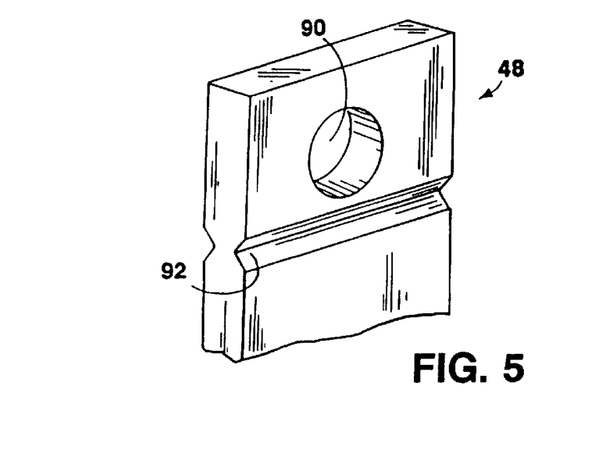
Figure 5A:
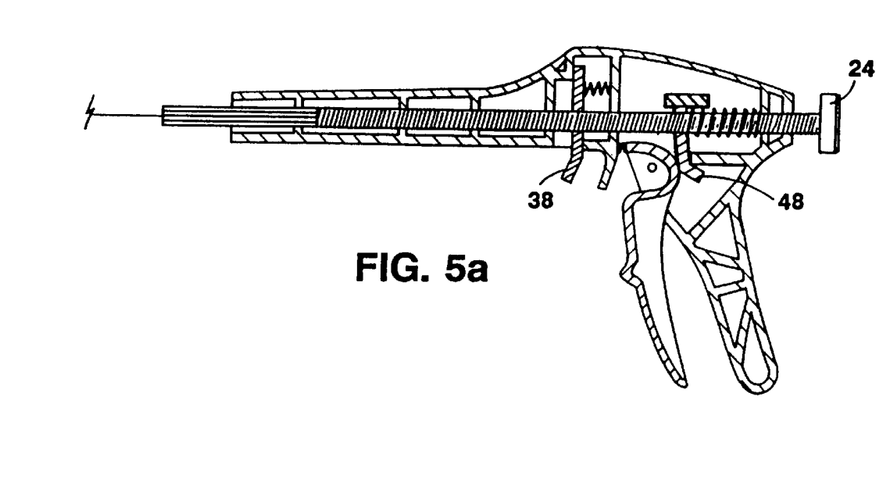
FIG. 5a illustrates use of the jam element in FIG. 5.

Referring to FIGS. 5 and 5a, in embodiments, the retractor key 48 can provide a tension limiting feature that prevents excessive tension from being placed on the basket, the wire, or the handle rod. The tension limiting feature is provided by the shape of the ratchet key 48, which includes an opening 90, through which the handle rod extends, and a narrow region 92 that bends at a predetermined stress.

Referring to FIG. 5a, as the assembly reaches the tension limit, the retracting key 48 bends at the narrow region into a different shape. In this shape, the trigger engages the retractor key for only approximately the last 20% of its stroke. The free motion of the trigger for most of the stroke indicates to the user that a hard calculus beyond the capability of the device has been encountered. The physician can continue to use the trigger over the last 20% of the stroke, but the shape of the key after bending limits the stroke of the handle rod so that further retraction is not possible and the tension limit cannot be exceeded. If the stroke reduces, signaling that a very hard calculus is present, the user can release the tension by pulling the trigger key 38. The control knob 24 can be used to project the basket from the sheath to disengage the calculus. Also, the user may, with the knob 24, rotate the basket to seek a more favorable orientation and the crushing operation can be attempted again. If the calculus cannot be crushed in this manner, the basket is disengaged from the calculus and the entire device can be removed from the body without disassembly. The patient may then be treated by other methods.

Other embodiments include mechanical advantage retraction mechanisms that provide greater or less than the 4 to 1 mechanical advantage provided by the trigger arrangement described above. For example, the rod may have a roughened outer surface or morphology that is complementary to engaging pieces that control rod motion. The device can be sized and constructed for use in organs besides the biliary tree. For example, the device can be used in other organs of the gastrointestinal tract. The operating assembly can be adapted for use with other types of graspers.

Still further embodiments are within the following claims.

What is claimed is:

1. An operating handle for a medical instrument, comprising:
   a housing,
   a control element extending along an axis,
   a manual actuator directly connected to said control element for moving said control element axially and for rotating said control element about the axis relative to said housing to a desired orientation, and
   a mechanical actuator coupled to said control element, said mechanical actuator being actuatable to move said control element axially with mechanical advantage and without rotation from said desired orientation.

2. The handle of claim 1 wherein said control element is adapted for being extended and withdrawn relative to a sheath.

3. A method of grasping an object in the body, comprising:

providing a medical instrument having an instrument axis and including a grasper actuatable between an open and closed condition, said medical instrument including a housing and an operating mechanism for actuating said grasper alternatively with mechanical advantage or without mechanical advantage and for rotating said grasper about said axis relative to said housing, positioning said grasper in proximity to said object, actuating said grasper to open said grasper, rotating said grasper to a desired orientation and manipulating said grasper about said object, and actuating said grasper with mechanical advantage to close said grasper.

4. The method of claim 3 comprising actuating said grasper with mechanical advantage without rotation of said grasper from said desired orientation.

5. The method of claim 3 or 4 comprising delivering said instrument through an endoscope.

6. The method of claim 5 wherein said object is a calculus.

* * * * *

UNITED STATES PATENT AND TRADEMARK OFFICE
CERTIFICATE OF CORRECTION

PATENT NO. : 5,957,932
DATED : September 28, 1999
INVENTOR(S) : Bates et al.

It is certified that error appears in the above-identified patent and that said Letters Patent is hereby corrected as shown below: On the title page: Item [56]

Under "References Cited - U.S. PATENT DOCUMENTS" on the cover page, the following reference should be inserted after the line referring to "4,945,920":

--5,057,114   10/1991   Wittich et al.--

Under "References Cited - U.S. PATENT DOCUMENTS" on the cover page, the following reference should be inserted after the line referring to "5,370,282":

--5,376,094   12/1994   Kline.--

Signed and Sealed this

Thirtieth Day of January, 2001

Attest:

Q. TODD DICKINSON

*Attesting Officer*     *Director of Patents and Trademarks*